United States Patent
Michelson et al.

(10) Patent No.: US 9,675,495 B2
(45) Date of Patent: Jun. 13, 2017

(54) CAPSULOTOMY INSTRUMENT

(76) Inventors: David Scott Michelson, La Jolla, CA (US); Tovy Sivan, Kfar-Saba (IL); Ido Kilemnik, Herzelia (IL)

( * ) Notice: Subject to any disclaimer, the term of this patent is extended or adjusted under 35 U.S.C. 154(b) by 2654 days.

(21) Appl. No.: 11/401,761

(22) Filed: Apr. 11, 2006

(65) Prior Publication Data

US 2006/0264990 A1  Nov. 23, 2006

Related U.S. Application Data

(60) Provisional application No. 60/670,705, filed on Apr. 13, 2005.

(51) Int. Cl.
- *A61F 9/013* (2006.01)
- *A61F 9/007* (2006.01)
- *A61B 17/00* (2006.01)

(52) U.S. Cl.
CPC ........ *A61F 9/0133* (2013.01); *A61F 9/00754* (2013.01); *A61B 2017/00867* (2013.01)

(58) Field of Classification Search
CPC .............. A61F 9/0133; A61F 9/00754; A61B 2017/00867
USPC ............... 606/169, 107, 166, 171, 167, 170; 433/119, 118; 30/277.4; 604/264, 22
See application file for complete search history.

(56) References Cited

U.S. PATENT DOCUMENTS

| | | | |
|---|---|---|---|
| 4,570,632 A | 2/1986 | Woods | |
| 4,911,161 A * | 3/1990 | Schechter | 606/107 |
| 5,269,787 A | 12/1993 | Cozean, Jr. et al. | |
| 5,275,607 A * | 1/1994 | Lo et al. | 606/169 |
| 5,437,678 A * | 8/1995 | Sorensen | 606/107 |
| 5,728,117 A | 3/1998 | Lash | |
| 5,904,690 A * | 5/1999 | Middleman et al. | 606/113 |
| 5,921,999 A * | 7/1999 | Dileo | 606/166 |
| 6,066,138 A | 5/2000 | Sheffer et al. | |
| 6,165,190 A | 12/2000 | Nguyen | |
| 6,371,294 B1 | 4/2002 | Blaustein et al. | |
| 6,551,326 B1 * | 4/2003 | Van Heugten et al. | 606/113 |
| 6,616,450 B2 * | 9/2003 | Mossle et al. | 433/119 |
| 6,629,980 B1 * | 10/2003 | Eibschitz-Tsimhoni | 606/107 |
| 6,845,537 B2 | 1/2005 | Wong | |
| 2004/0116952 A1 * | 6/2004 | Sakurai et al. | 606/169 |

FOREIGN PATENT DOCUMENTS

WO  WO 2006/109255  10/2006

* cited by examiner

*Primary Examiner* — Corrine McDermott
*Assistant Examiner* — Tin Nguyen
(74) *Attorney, Agent, or Firm* — Joshua C. Harrison, Esq.; Barcelo, Harrison & Walker, LLP

(57) ABSTRACT

A capsulotomy cutting device includes a planar cutting head sized to fit into intraocular tissue. The planar cutting head includes at least one sharp edge and an oscillation mechanism adapted to oscillate the cutting head. Capsulotomy is achieved by inserting the planar cutting head through an incision in the eyeball, placing the cutting edge of the cutting head against the tissue of the lens capsule therein, and then oscillating the cutting head by an oscillation mechanism coupled to the cutting head.

15 Claims, 4 Drawing Sheets

CAPSULOTOMY INSTRUMENT

RELATED APPLICATIONS

The present application claims the benefit under 119(e) of U.S. provisional patent application 60/670,705, filed Apr. 13, 2005, the disclosure of which is incorporated herein by reference.

FIELD OF THE INVENTION

The present invention relates to eye surgery and particularly to anterior capsulotomy.

BACKGROUND OF THE INVENTION

The human eye includes a lens enclosed by a transparent capsule. Cataract is a condition characterized by opacity of the lens causing partial or total blindness. Cataracts are treated by removal of the defective lens and replacement with an artificial lens. An initial step of cataract surgery is an anterior capsulotomy, wherein an opening is made in the outer capsule to allow the removal of the defective lens.

The most common method of performing a capsulotomy is to rupture the capsule with a needle, in order to create a tear. The surgeon then grasps the free edge of the tear with either forceps or the needle and maneuvers, by manual dexterity, to create an approximately circular opening in the center of the capsule. Performing a capsulotomy with needle and forceps is difficult and the results are neither uniform nor predictable. This non-uniformity of the result is a disadvantage, because the success of the capsulotomy dictates to a large extent the quality and success of the entire cataract operation.

In order to access the capsule for the capsulotomy, an opening must be made in the cornea or sclera, which are layers of the eye external to the lens capsule. Fast recovery of the cornea or sclera is aided when the access opening has a minimal size. Therefore, the surgical manipulations of the capsulotomy are generally performed through an access wound in the cornea or sclera, which is expected to be no greater than 3.0 mm in length and 0.1 mm in height. Though the tissue in the cornea and sclera is somewhat distensible, it currently accommodates instruments no greater than 0.75 mm in height. As cataract surgery instrumentation advances, entrance wounds are being made smaller and smaller, in order to shorten the post operative recovery period.

U.S. Pat. No. 6,165,190 to Nguyen, the disclosure of which is incorporated herein by reference, describes a capsulectomy device having a needle that rotates up and down radially relative to the eye lens capsule, in order to cut the capsule. The needle is mounted on a rotating arm that controls the radius of the cut in the capsule. The radial rotation of the needle requires space, which may not be easily available in capsulectomy procedures.

U.S. Pat. No. 6,551,326 to Van Heugten et al., the disclosure of which is incorporated herein by reference, describes a capsulorrhexis device having a super elastic rod that is entered into the eye and formed into a circular loop with a desired radius. The rod cuts the eye lens capsule when it is retracted from the eye. This device may have problems of accurate operation and mechanical failure.

U.S. Pat. No. 6,629,980 to Eibschitz-Tsimhoni, the disclosure of which is incorporated herein by reference, describes an eye lens capsule cutting device having a curvilinear head portion. The force required by a physician in order to cut a hole in the capsule using such a cutting device is large, such that the physician is required to apply a substantial force in an accurate manner, in order to achieve the cutting, without cutting too deep into the eye and damaging the eye.

U.S. Pat. No. 6,066,138 to Sheffer et al., the disclosure of which is incorporated herein by reference, describes a medical instrument for burning a lens capsule of an eye.

U.S. Pat. No. 5,728,117 to Lash, the disclosure of which is incorporated herein by reference, describes a capsulorrhexis instrument that is retractable within a tube and extendable into a position projecting out of the tube. In the position out of the tube, the instrument has a circular shape with a sharp blade for cutting a hole in the capsule.

SUMMARY OF THE INVENTION

An aspect of an embodiment of the invention relates to a capsulotomy cutting device having a planar cutting head and a handle adapted to oscillate the cutting head. The term planar cutting head refers herein to a cutting head whose points adapted to come in contact with a surface to be cut are not concentrated around a single point and are not included in a single straight line. The handle optionally oscillates the cutting head along an axis tangent to a plane of the cutting head and hence tangent to the lens capsule. The oscillation optionally is performed in small steps, which achieve the cutting of a planar cut in the lens capsule. The oscillation achieves a relatively smooth cut, which allows a safer and more predictable cut, which can be more accurately controlled and customized by the surgeon.

Optionally, the planar cutting head has a convex shape. In some embodiments of the invention, the cutting head has a curvilinear shape.

In some embodiments of the invention, the cutting head has sharp edges on two planar sides, such that it can be easily used for cutting both right and left opening curvilinear cuts, by simply turning over the cutting head. Optionally, the cutting head is small enough to allow turning over of the cutting head within the anterior chamber of the patient's eye.

There is therefore provided in accordance with an exemplary embodiment of the invention, a capsulotomy cutting device, comprising a planar cutting head sized to fit into intraocular tissue, including at least one sharp edge and an oscillation mechanism adapted to oscillate the cutting head.

Optionally, the at least one sharp edge comprises a pair of edges on opposite surfaces of the cutting head. Optionally, the planar cutting head comprises a convex cutting head. Optionally, the planar cutting head comprises a curvilinear cutting head. Optionally, the cutting head is semicircular. Optionally, the cutting head has a shape of half of an ellipse. Optionally, the sharp edge spans over at least 135°. Optionally, the sharp edge has a diameter of between about 3-9 millimeters. Optionally, the cutting head has a shape adjustable within intraocular tissue. Optionally, the cutting head comprises a super elastic material. Optionally, the oscillation mechanism oscillates at a rate of at least 10 Hz. Optionally, the oscillation mechanism comprises an eccentric motor and/or is driven by a piezoelectric crystal.

Optionally, the cutting head is held on a handle and the oscillation mechanism oscillates the cutting head along a longitudinal axis of the handle. Optionally, the cutting device is removably coupled to the oscillation mechanism. Optionally, the at least one sharp edge has a length of more than 1 mm.

Optionally, the cutting device includes a removable cover adapted to cover the cutting head and to be removable within intraocular tissue. Optionally, the cutting device includes a pivot coupled to the cutting head, allowing controllable rotation of the cutting head.

There is further provided in accordance with an exemplary embodiment of the invention, a method of cutting an incision in internal body tissue, comprising inserting a planar cutting head through an incision in body tissue, placing a cutting edge of the cutting head against tissue, and oscillating the cutting head, by an oscillation mechanism coupled to the cutting head.

Optionally, the cutting edge has a larger diameter than the incision through which the cutting head is inserted. Optionally, the cutting edge has a first configuration when it is inserted through the incision and a second configuration when placed against tissue.

Optionally, the cutting head is compressed to a thin straight line in the first configuration. Optionally, the cutting edge has a same configuration when inserted through the incision and when placed against tissue.

BRIEF DESCRIPTION OF FIGURES

Particular non-limiting exemplary embodiments of the invention will be described with reference to the following description of embodiments in conjunction with the figures. Identical structures, elements or parts which appear in more than one figure are preferably labeled with a same or similar number in all the figures in which they appear, in which.

DETAILED DESCRIPTION OF EMBODIMENTS

Figures 1, 2:
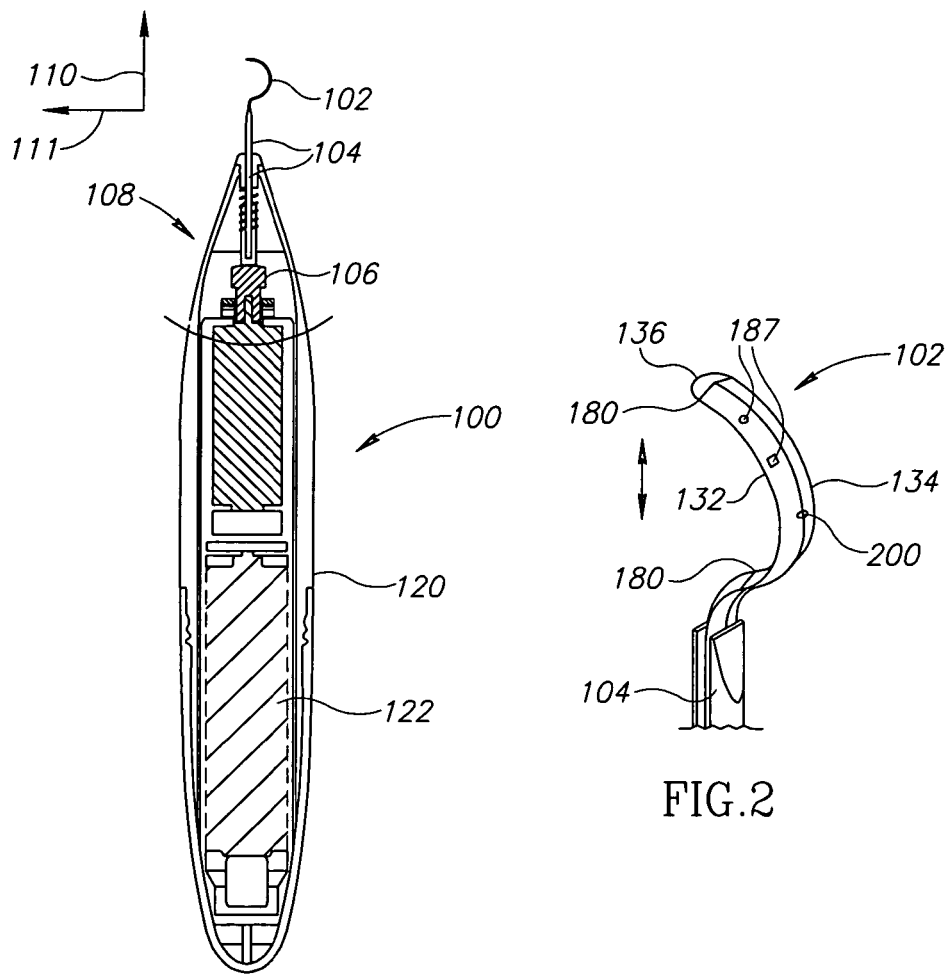
FIG. 1 is a cross-sectional view of a capsulotomy cutting device, in accordance with an exemplary embodiment of the invention.
FIG. 2 is an enlarged view of a cutting head, in accordance with an exemplary embodiment of the invention.

FIG. 1 is a cross-sectional view of a capsulotomy cutting device 100, in accordance with an exemplary embodiment of the invention. Cutting device 100 includes a cutting head 102 connected through a handle 104 to an oscillation mechanism 108, which moves cutting head 102 back and forth in an axial direction, defined by the long axis of cutting device 100, indicated by arrow 110. The movement of cutting head 102 in direction 110 when placed on tissue achieves a cut in the tissue, in the shape of cutting head 102. In some embodiments of the invention, a housing 120 serves as a handle of cutting device 100. In addition, housing 120 optionally hosts batteries 122, which power oscillation mechanism 108. A switch, button or any other control (not shown) mounted on housing 120 is used to control the operation of oscillation mechanism 108.

Cutting Head

FIG. 2 is an enlarged perspective view of cutting head 102, in accordance with an exemplary embodiment of the invention. Cutting head 102 optionally has a semicircular shape for cutting a circular or semi-circular incision in the lens capsule. Cutting head 102 optionally has sharp edges 132 and 134 on both planar sides of the cutting head, such that cutting can be performed on either planar side of the cutting head.

In cutting a circular or a semi-circular hole in eye tissue, cutting head 102 is placed in the eye tissue with first sharp edge 134 placed against a surface to be cut. Thus, at a single time, a substantial portion (e.g., more than 25% or even more than 35%) of the length of the lens capsule which needs to be cut, e.g., more than 1-2 mm, is in contact with the sharp edge. Oscillation mechanism 108 is then operated until a cut in the size and shape of sharp edge 134 is achieved. Cutting head 102 is then turned over, such that second sharp edge 132 is placed against tissue to be cut. Oscillation mechanism 108 is then re-operated, so that a cut of the size and shape of sharp edge 134 is achieved.

Figure 3A:
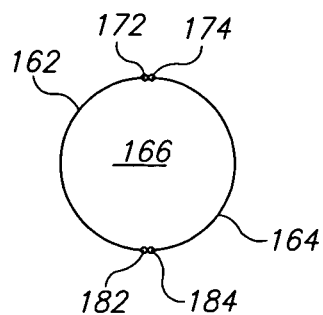
FIGS. 3A-3C are schematic illustrations of possible relative positions of cuts made by a cutting device, in accordance with an exemplary embodiment of the invention.
Figure 3B:
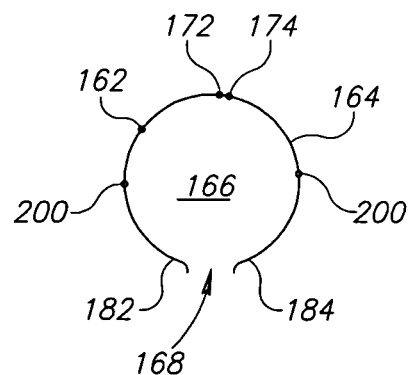
Figure 3C:
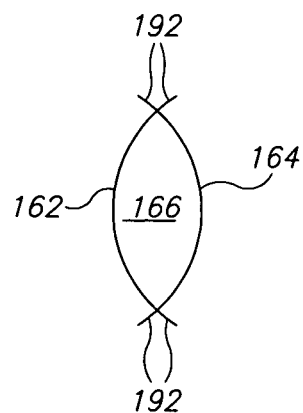

FIGS. 3A-3C are schematic illustrations of openings in the anterior chamber achieved using cutting device 100, in accordance with exemplary embodiments of the invention. As shown in FIG. 3A, first and second cuts 162 and 164, achieved by sharp edges 132 and 134, respectively, define an incision 166. A top end 172 (in FIG. 3A) and a bottom end 182 of cut 162 substantially coincide with top and bottom ends 174 and 184 of cut 164, such that incision 166 is completely cut out of the underlying tissue and cuts 162 and 164 do not substantially extend into tissue not included in incision 166.

In FIG. 3B, the top ends 172 and 174 of cuts 162 and 164 substantially coincide, while the bottom ends 182 and 184 leave an uncut gap 168 between them. Optionally, the uncut gap 168 is not cut out in the cutting procedure, but rather is allowed to remain for the healing process. Alternatively, the uncut gap 168 is removed at a later stage using a third application of cutting head 102 or using any other cutting tool. In FIG. 3B, the incision 166 is larger than in FIG. 3A, due to gap 168.

In FIG. 3C, cuts 162 and 164 intersect, such that the cuts include external portions 192 that extend beyond that required in order to cut out incision 166. Generally, external portions 192 heal naturally and do not cause complications in the eye. In FIG. 3C, incision 166 is smaller than in FIG. 3A, due to the intersection of the cuts 162 and 164.

By selecting a relative layout of cuts 162 and 164, a physician determines a desired size and shape of incision 166. Thus, a single cutting device 100 can be used to form incisions 166 of a plurality of different sizes. Referring to a farthest point 200 from the longitudinal axis of cutting device 100, the distance between point 200 in cuts 162 and 164 defines, in some embodiments of the invention, the size and shape of incision 166. Optionally, markings 187 along cutting head 102 aid the physician in positioning the second sharp edge (e.g., 132) relative to the first cut (e.g., 164) in order to achieve a cut of a desired size. Alternatively or additionally, cutting head 102 includes visible markings 180, which identify the end points of sharp edges 132 and 134.

Sharp edges 132 and 134 optionally extend over substantially the entire extent of cutting head 102. In some embodiments of the invention, sharp edges 132 and 134 do not extend over a distal tip 136 of cutting head 102, so that distal tip 136 does not cause inadvertent cutting when inserted into the patient's eye. Alternatively, sharp edges 132 and/or 134 extend over the entire distal tip 136 of cutting head 102. In some embodiments of the invention, sharp edges 132 and 134 do not extend to a connection point of cutting head 102 with handle 104, so as to limit the chance of inadvertent undesired cutting. In an exemplary embodiment of the invention, sharp edges 132 and 134 extend over about 145°-165°. Alternatively, sharp edges 132 and 134 extend over at least 180°, so that a complete circle cut can be made when a circular cut of a maximal radius of cutting head 102 is desired.

In some embodiments of the invention, sharp edges 132 and 134 have a same extent. Alternatively, sharp edges 132 and 134 have different extents, allowing formation of unsymmetrical cuts, when required.

The size of cutting head 102 is optionally a compromise between a large size for achieving large cutting edges and a small size which is easier to manipulate in the anterior chamber. In some embodiments of the invention, cutting head 102 extends over about half a circle, e.g., about 175°-185°, such that a distal tip 136 of cutting head 102 is substantially on the longitudinal axis of cutting device 100.

Cutting Head Size

In some embodiments of the invention, the semi-circular portion of cutting head 102 has a diameter of between about 6.5-7.5 millimeters. Cutting head 102 is optionally larger than the size of a required incision, by between about 10-20%, or even 40-50%, as the area of the cut is defined by the crossing of the curved lines cut out by both of sharp edges 132 and 134. Alternatively, cutting head 102 has a smaller size, optionally having a diameter smaller than 5 millimeters or even smaller than 2 millimeters. In an exemplary embodiment of the invention, cutting head 102 has a diameter of between about 0.5-1.5 millimeters. Such small cutting heads are optionally used in procedures in which the lens of the eye is removed by liquidification or partial liquidification and therefore only a small incision is required.

Oscillation

Figure 4:
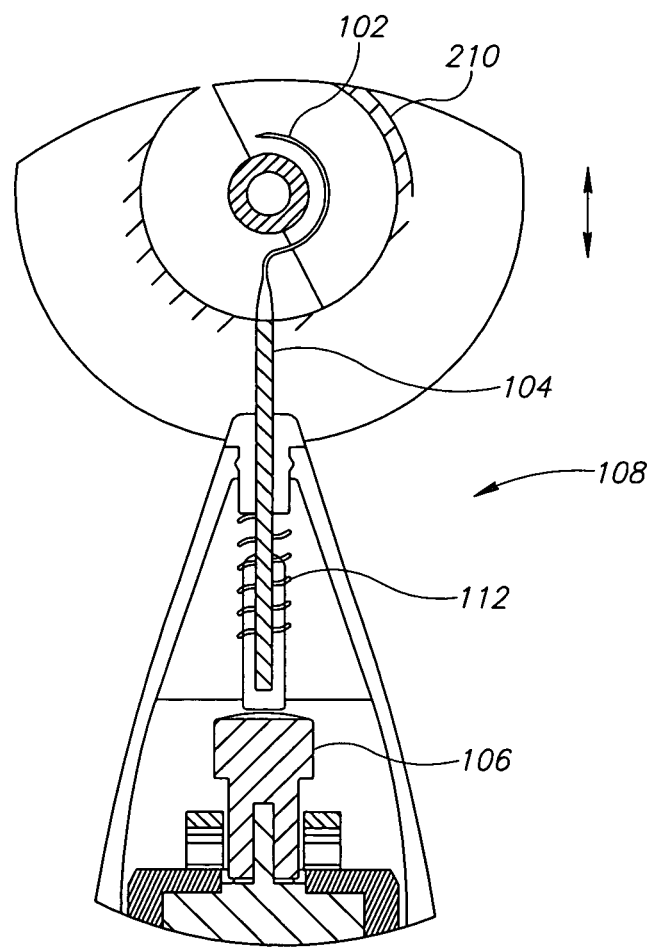
FIG. 4 is an enlarged cross-sectional view of the capsulotomy cutting device of FIG. 1 placed against an eye, in accordance with an exemplary embodiment of the invention.

FIG. 4 is an enlarged view of oscillation mechanism 108 and cutting head 102 placed against an eye 210, in accordance with an exemplary embodiment of the invention. Oscillation mechanism 108 optionally comprises a motor 106 which pushes cutting head 102 distally, and a spring 112, which retracts cutting head 102 proximally, so as to generate the oscillating movement. Optionally, motor 106 includes a piezoelectric crystal. Alternatively or additionally, any oscillation method and/or apparatus known in the art, may be used for inducing the oscillations of cutting head 102, for example apparatus used for power-driven toothbrushes. Some of such mechanisms are described, for example, in U.S. Pat. No. 6,845,537 to Wong and/or U.S. Pat. No. 6,371,294 to Blaustien et al., the disclosures of which are incorporated herein by reference.

Alternatively or additionally, motor 106 comprises a small eccentric motor (e.g., a motor with an off-axis weight) with an attached mass which moves the center of mass of the motor away from the central axis of the motor. Further alternatively or additionally, an oscillation mechanism as used in portable cellular telephones is used instead of or in addition to motor 106.

In some embodiments of the invention, cutting head 102 oscillates at a rate of at least 10 Hz, or even at least 20 Hz. Optionally, cutting head 102 oscillates at a rate of less than 100 Hz, less than 50 Hz or even less than 30 Hz. Alternatively, cutting head 102 oscillates at higher or lower rates. In some embodiments of the invention, the rate of oscillation of cutting head 102 is adjustable by a physician, according to personal preferences and/or the texture of tissue being cut. The oscillation rate is optionally selected to achieve the cut of the tissue while requiring from a physician minimal pressure of the cutting head against the tissue.

The amplitude of the oscillations of cutting head 102 is optionally at least 0.02 mm or even at least 0.1 mm. In some embodiments of the invention, the amplitude of the oscillations is smaller than 1 millimeter or even smaller than 0.5 millimeters. In an exemplary embodiment of the invention, the amplitude of the oscillations is smaller than 0.2 millimeters.

Possibly, those portions of cutting head 102 which are relatively parallel to the direction 110 of oscillation, operate as a saw when the oscillating is performed. The parallel portions generally cut into the tissue in a first stage of the cutting. The movement of the parallel portions of cutting head 102 downward into the cut tissue, possibly causes the portions of cutting head 102 that are perpendicular to the oscillation to cut into the tissue as they decline into the tissue with the parallel portions.

Alternatively or additionally to oscillating along the axis of cutting device 100, cutting head 102 oscillates in other directions, for example in a direction indicated by an arrow 111, in the plane of the axis of cutting device 100 perpendicular to the axis. In some embodiments of the invention, the oscillation is in a diagonal direction, for example 45° to the axis of the cutting device. In some embodiments of the invention, the direction of the oscillation changes during a cutting procedure, so that different portions of cutting head 102 have a saw effect on the tissue. In some embodiments of the invention, cutting head 102 oscillates in a direction normal to the cut surface, or in a diagonal direction having a component normal to the cut surface.

Cutting Head Shape

Cutting head 102 has a shape that defines an incision having a substantial area. Optionally, cutting head 102 is defined as a portion of a substantially perfect circle. Alternatively, in order to achieve a non-circular cut, a semi-elliptical (e.g., half an ellipse) cutting head is used. Further alternatively, a triangular or rectangular shape, or any other shape is used for cutting head 102. In some embodiments of the invention, cutting head 102 is formed from a relatively soft material or structure, which allows a physician to adjust the shape of cutting head 102. Optionally, cutting head 102 is relatively rigid in the cutting direction, while being relatively flexible in a direction allowing adjustment of the planar shape of the cutting head.

In some embodiments of the invention, rather than having an open shape, cutting head 102 has a closed shape, such as a full circle or elliptic shape. Optionally, the cutting head in accordance with this embodiment has a flexible shape which can be condensed for insertion into the eye. After insertion, the cutting head is expanded to its cutting shape, for example as described in above mentioned U.S. Pat. No. 5,728,117. After the expanding of the cutting head, the cutting head is oscillated to perform the cutting.

In an exemplary embodiment of the invention, cutting head 102 comprises a super elastic rod that is entered into the eye and formed into a predetermined shape within the eye. After the predetermined shape is formed, the oscillation is activated. In some embodiments of the invention, the predetermined shape comprises a circle with a predetermined radius, such as described in above mentioned U.S. Pat. No. 6,551,326.

Alternatively or additionally, any other method of adjusting the shape of the cutting head within the eye is performed before applying the oscillation.

Protective Cover

In some embodiments of the invention, a protective cover (not shown) is slid over cutting head 102 when not in use. Alternatively or additionally, the protective cover covers cutting head 102, while the cutting head is maneuvered into the patient's anterior chamber. In some embodiments of the invention, the cover is connected to a control on housing 120, which allows a physician to remove the cover, while cutting head 102 is within the anterior chamber. Alternatively or additionally, the physician can move the cover back onto cutting head 102, while cutting head 102 is within the anterior chamber. Optionally, the control comprises a thin string running along or within housing 120. Alternatively, any other mechanism, such as described below in relation to FIG. 5, is used.

In some embodiments of the invention, cutting head 102 and handle 104 are permanently mounted on housing 120. Alternatively, housing 120 includes a receptacle adapted to receive a manual prior art cutting device and to provide oscillation to the cutting head. Further alternatively, handle 104 detachably connects to cutting head 102, allowing, for example, mounting of different size cutting heads 102 on handle 104 and/or replacement for sterilization of the cutting heads.

Figure 5:
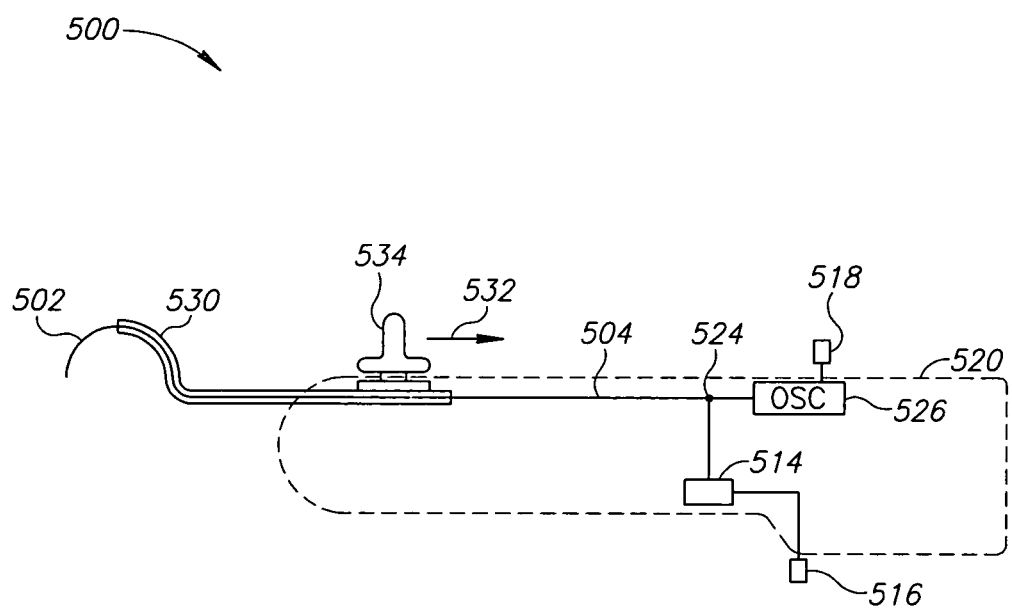
FIG. 5 is a schematic sectional view of a capsulotomy cutting device, in accordance with another exemplary embodiment of the invention.

Alternatively to requiring that a physician turn over the cutting head by turning over cutting device 100, an automatic mechanism is provided within cutting device 100 for flipping the cutting head, as is now described in relation to FIG. 5.

FIG. 5 is a schematic sectional view of a capsulotomy cutting device 500, in accordance with an exemplary embodiment of the invention. Cutting device 500 comprises a cutting head 502 with a handle 504 extending within a housing 520. A blade cover 530 is used to cover a blade of cutting head 502 and hence prevent inadvertent cutting by the blade. As shown, blade cover 530 is half employed, covering only a proximal half of cutting head 502. A cover manipulation handle 534 is moved axially in parallel to handle 504, in order to remove blade cover 530 from covering cutting head 502 and/or in order to cover cutting head 502. Moving handle 534 proximally, as indicated by an arrow 532, exposes the blades of cutting head 502 for cutting, while moving handle 534 distally, in the direction opposite that indicated by arrow 532, conceals the blade of cutting head 502. Blade cover 530 optionally comprises a semi-rigid plastic, which on the one hand moves without folding over itself, and on the other hand can follow the contours of cutting head 502. Alternatively, blade cover 530 is formed of any other material that allows movement back and forth to conceal and expose the blades of cutting head 502.

In some embodiments of the invention, cutting head 502 is inserted into the patient's eye with blade cover 530 completely covering cutting head 502. When cutting head 502 is in place, blade cover 530 is retracted and the cutting is performed. When the cutting is completed, blade cover 530 is moved back to cover cutting head 502 and the cutting head is removed from the patient's eye. In some embodiments of the invention, cutting head 502 is also covered before flipping cutting head 502 within the patient's eye. Alternatively, blade cover 530 can be moved within the patient's eye only proximally (or only distally). In accordance with this alternative, the production of blade cover 530 is simpler.

An oscillation motor 526 optionally oscillates cutting head 502 under control of a button (or other control) 518.

In some embodiments of the invention, a pivot 524 controlled by a rotation motor 514 is used by the physician to rotate handle 504 and hence cutting head 502. In some embodiments of the invention, the rotation of pivot 524 is used to flip cutting head 502, instead of turning housing 520. Optionally, rotation motor 514 is actuated by a button 516. In some embodiments of the invention, the actuating of button 516 causes pivot 524 to rotate 180°. Alternatively, actuating of button 516 causes pivot 524 to rotate in small steps (e.g., 15°, 30°, 45°, 60°), allowing the physician to control the angle of the cutting head. Further alternatively, pivot 524 rotates in a continuous manner when button 516 is actuated.

Alternatively to a rotation motor 514, pivot 524 is controlled mechanically, for example by a lever directly attached to pivot 524, which is rotated by the physician. In some embodiments of the invention, rather than being battery operated, cutting head 102 is operated by a power cable or other energy source.

While the above description relates to a capsulotomy cutting device, the device of the present invention may be used to cut tissue in other body organs, such as the brain, head or neck, especially where it is desired to cut a circular, semi-circular or other planar cut beneath tissue, using an access hole smaller than the desired cut.

It will be appreciated that the above described methods of using the cutting device may be varied in many ways, including performing three or more cuts in achieving an incision. In some embodiments of the invention, however, a complete incision is achieved with no more than ten or even five placements of cutting head 102 against different locations on the lens capsule. It should also be appreciated that the above described description of methods and apparatus are to be interpreted as including apparatus for carrying out the described methods and methods of using the described apparatus.

The present invention has been described using non-limiting detailed descriptions of embodiments thereof that are provided by way of example and are not intended to limit the scope of the invention. It should be understood that features and/or steps described with respect to one embodiment may be used with other embodiments and that not all embodiments of the invention have all of the features and/or steps shown in a particular figure or described with respect to one of the embodiments. Variations of embodiments described will occur to persons of the art.

It is noted that some of the above described embodiments may describe the best mode contemplated by the inventors and therefore may include structure, acts or details of structures and acts that may not be essential to the invention and which are described as examples. Structure and acts described herein are replaceable by equivalents which perform the same function, even if the structure or acts are different, as known in the art. Therefore, the scope of the invention is limited only by the elements and limitations as used in the claims. When used in the following claims, the terms "comprise", "include", "have" and their conjugates mean "including but not limited to".

The invention claimed is:

1. A capsulotomy cutting device for cutting a lens capsule, the device comprising:
    a planar cutting head for cutting the lens capsule, the planar cutting head sized to fit into intraocular tissue, the planar cutting head consisting of one blade, the capsulotomy cutting device not including any other blade, the one blade including at least two sharp edges in a fixed spatial relationship to each other, the at least two sharp edges being on opposite surfaces of the planar cutting head;
    an oscillation mechanism coupled to the one blade and that oscillates the one blade at a rate less than 100 Hz; and
    a pivot that allows relative rotation of the one blade with respect to the oscillation mechanism during operation of the capsulotomy cutting device, without decoupling the one blade from the oscillation mechanism.

2. The capsulotomy cutting device according to claim 1, wherein the planar cutting head comprises a convex cutting head.

3. The capsulotomy cutting device according to claim 1, wherein the planar cutting head comprises a curvilinear cutting head.

4. The capsulotomy cutting device according to claim 1, wherein the planar cutting head is semicircular.

5. The capsulotomy cutting device according to claim 1, wherein the planar cutting head has a shape of half of an ellipse.

6. The capsulotomy cutting device according to claim 1, wherein each of the at least two sharp edges spans over at least 135 degrees.

7. The capsulotomy cutting device according to claim 1, wherein each of the at least two sharp edges has a diameter of between about 3-9 millimeters.

8. The capsulotomy cutting device according to claim 1, wherein the oscillation mechanism oscillates at a rate of at least 10 Hz.

9. The capsulotomy cutting device according to claim 1, wherein the oscillation mechanism is driven by a piezoelectric crystal.

10. The capsulotomy cutting device according to claim 1, wherein the oscillation mechanism comprises an eccentric motor.

11. The capsulotomy cutting device according to claim 1, wherein the planar cutting head is held on a handle and the oscillation mechanism oscillates the planar cutting head along a longitudinal axis of the handle.

12. The capsulotomy cutting device according to claim 1, wherein the one blade is removably coupled to the oscillation mechanism.

13. The capsulotomy cutting device according to claim 1, wherein each of the at least two sharp edges has a length of more than 1 mm.

14. The capsulotomy cutting device according to claim 1, comprising a removable cover adapted to cover the cutting head and to be removable within intraocular tissue.

15. A method of cutting an incision in a lens capule within an eyeball, comprising;
   inserting a planar cutting head through an incision in the eyeball, the planar cutting head consisting of one blade, the planar cutting head not including any other blade, the one blade including first and second cutting edges in a fixed spatial relationship to each other, the first cutting edge being on an opposing surface of the planer cutting head from the second cutting edge;
   placing the first cutting edge against tissue of the lens capsule; and
   oscillating the planer cutting head at a rate less than 100 Hz by an oscillation mechanism coupled to the planer cutting head for cutting the incision in the lens capsule;
   wherein the first cutting edge has a first shape when it is inserted through the incision and a second shape when placed against tissue, the second shape being different from the first shape; and
   wherein the first cutting edge has a larger diameter than the incision through which the planar cutting head is inserted.

* * * * *